US00PP34150P3

(12) United States Plant Patent
Post

(10) Patent No.: US PP34,150 P3
(45) Date of Patent: Apr. 19, 2022

(54) ***CHRYSANTHEMUM* PLANT NAMED 'DLFHOLA6'**

(50) Latin Name: ***Chrysanthemum* X *morifolium***
Varietal Denomination: DLFHOLA6

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/395,279

(22) Filed: Aug. 5, 2021

(65) Prior Publication Data

US 2022/0046843 P1 Feb. 10, 2022

Related U.S. Application Data

(60) Provisional application No. 63/062,375, filed on Aug. 6, 2020.

(51) Int. Cl.
*A01H 5/02* (2018.01)
*A01H 6/14* (2018.01)

(52) U.S. Cl.
USPC ..... Plt./296

(58) Field of Classification Search
USPC ..... Plt./263.1, 284, 286, 296
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Chrysanthemum* plant named 'DLFHOLA6', characterized by its upright plant habit; vigorous growth habit; dark green-colored leaves; uniform and freely flowering habit; strong upright flowering stems; anemone-type inflorescences with bright orange yellow-colored ray florets; resistance to *Fusarium*; relative tolerance to low and high production temperatures; and excellent postproduction longevity.

2 Drawing Sheets

Botanical designation: *Chrysanthemum* X *morifolium.*

Figure 1:
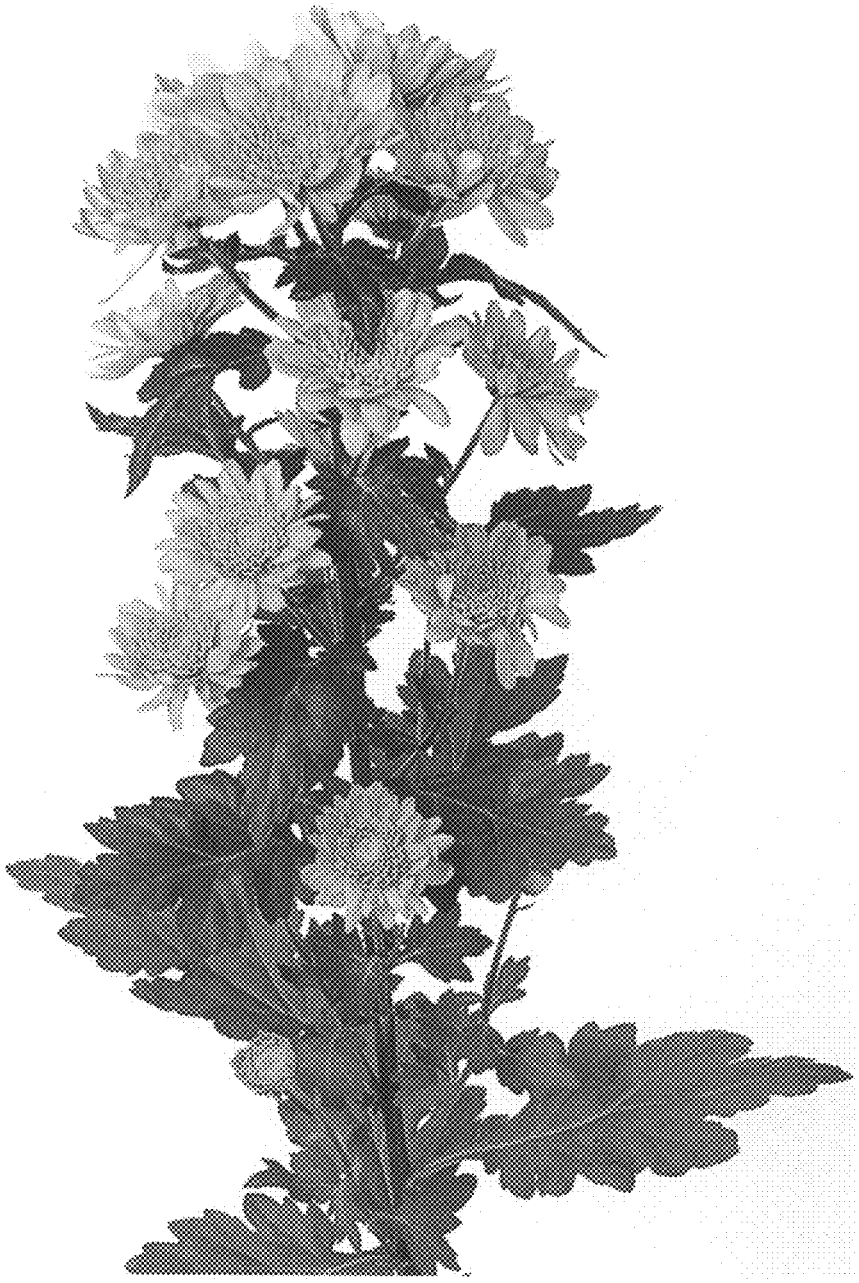

Cultivar denomination: 'DLFHOLA6'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Jul. 16, 2020. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFHOLA6'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in April, 2017 of a proprietary selection of *Chrysanthemum* x *morifolium* identified as code number db 56143, not patented, as the female, or seed, parent with a proprietary selection of *Chrysanthemum* x *morifolium* identified as code number db 91495, not patented, as the male, or pollen, parent. The new *Chrysanthemum* plant was discovered and selected as a single flowering plant from within the progeny of the stated cross-pollination in a controlled greenhouse environment in Maasdijk, The Netherlands in February, 2018.

Asexual reproduction of the new *Chrysanthemum* plant by vegetative terminal cuttings since February, 2018 in a controlled greenhouse environment in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFHOLA6'. These characteristics in combination distinguish 'DLFHOLA6' as a new and distinct *Chrysanthemum* plant:

1. Upright plant habit; vigorous growth habit.
2. Dark green-colored leaves.
3. Uniform and freely flowering habit.
4. Strong upright flowering stems.
5. Anemone-type inflorescences with bright orange yellow-colored ray florets.
6. Resistant to *Fusarium* (*Fusarium oxysporum*).
7. Relatively tolerant to low and high production temperatures.
8. Excellent postproduction longevity.

Plants of the new *Chrysanthemum* differ primarily from plants of the female parent selection in ray floret color as ray florets of plants of the new *Chrysanthemum* are bright orange yellow in color whereas ray florets of plants of the female parent selection are white in color. In addition, ray florets apices of plants of the new *Chrysanthemum* are shallowly emarginate to close to obtuse whereas ray florets apices of plants of the female parent selection are rounded.

Plants of the new *Chrysanthemum* differ primarily from plants of the male parent selection in ray floret color as ray florets of plants of the new *Chrysanthemum* are bright orange yellow in color whereas ray florets of plants of the male parent selection are white in color. In addition, ray florets apices of plants of the new *Chrysanthemum* are shallowly emarginate to close to obtuse whereas ray florets apices of plants of the male parent selection are mammillate.

Plants of the new *Chrysanthemum* can be compared to plants of *Chrysanthemum* X *morifolium* 'DLFAPPE6', not patented. In side-by-side comparisons, plants of the new *Chrysanthemum* differ primarily from plants of 'DLFAPPE6' in ray floret color as ray florets of plants of the new *Chrysanthemum* are more orange than and not as yellow in color as ray florets of plants of 'DLFAPPE6'. In addition, fully opened ray florets of plants of the new *Chrysanthemum* are mostly straight whereas fully opened ray florets of plants of 'DLFAPPE6' are incurved.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) comprises a side perspective view of a typical flowering stem of 'DLFHOLA6' grown as a spray-type cut flower.

Figure 2:
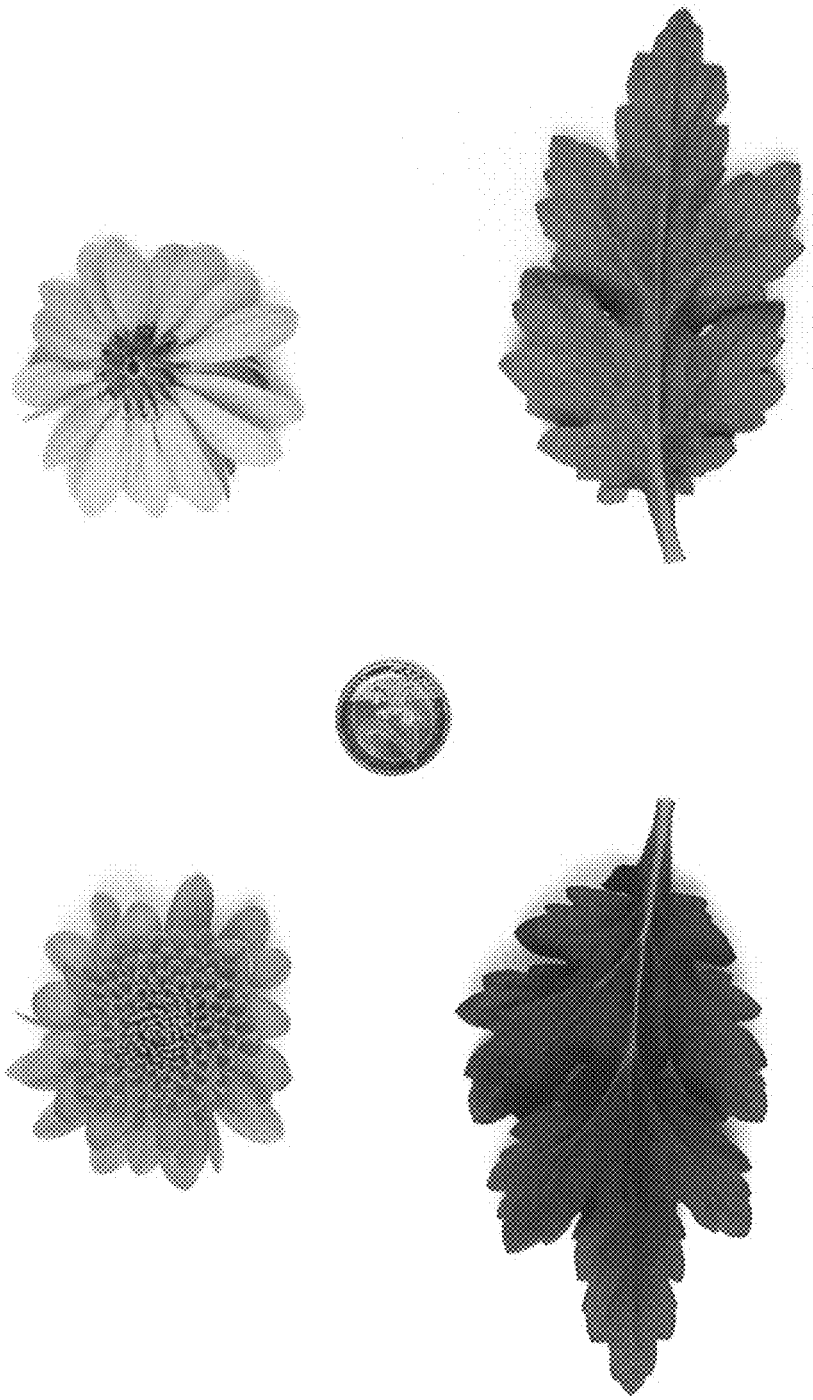

The photograph on the second sheet (FIG. 2) is a close-up view of upper (left) and lower (right) surfaces of typical leaves (bottom of photographic sheet) and inflorescences (top of photographic sheet).

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were ten weeks old when the photographs were taken and eleven weeks old when the description was taken. In the following description, color references are made to The Royal Horticultural Society Colour Chart, 2015 Edition, except where general terms of ordinary dictionary significance are used.

Botanical classification: *Chrysanthemum* X *morifolium* 'DLFHOLA6'.

Parentage:

*Female, or seed, parent*.—Proprietary selection of *Chrysanthemum* x *morifolium* identified as code number db 56143, not patented.

*Male, or pollen, parent*.—Proprietary selection of *Chrysanthemum* x *morifolium* identified as code number db 91495, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous anemone-type cut flower that is typically grown as a single stem spray-type; upright plant habit; vigorous growth habit and rapid growth rate.

*Plant height, soil level to top of foliar plane*.—About 68.3 cm.

*Plant height, soil level to top of inflorescence plane*.—About 74.6 cm.

*Plant (spray) diameter*.—About 21.8 cm.

*Flowering stem length*.—About 67.3 cm.

*Flowering stem diameter*.—About 7.5 mm.

*Flowering stem internode length*.—About 2.1 cm.

*Flowering stem strength*.—Strong.

*Flowering stem aspect*.—Erect.

*Flowering stem texture and luster*.—Densely pubescent; slightly glossy.

*Flowering stem color, developing*.—Close to 146D.

*Flowering stem color, developed*.—Close to 146B and 148B.

*Leaf description*.—Arrangement: Alternate; simple. Length: About 13.5 cm. Width: About 8.6 cm. Shape, in overall outline: Ovate to oblong. Apex: Abruptly acute, minute. Base: Attenuate. Margin: Palmately lobed, coarsely crenate; sinuses convergent with lobes slightly imbricate; sinuses medium in depth to deep. Texture and luster, upper surface: Densely pubescent, not rugose; moderately velvety; matte. Texture and luster, lower surface: Densely pubescent, prominent venation; slightly velvety; slightly glossy. Venation pattern: Pinnate, reticulate. Color: Developing leaves, upper surface: Close to 137C. Developing leaves, lower surface: Close to 138B. Fully developed leaves, upper surface: Close to NN137A to NN137B; venation, close to 147C. Fully developed leaves, lower surface: Close to 147B; venation, close to 148C. Petioles: Length: About 1.5 cm. Diameter: About 4 mm by 4 mm. Strength: Moderately strong. Texture and luster, upper and lower surfaces: Densely pubescent; moderately glossy. Color, upper surface: Close to 148C; edges close to 137B. Color, lower surface: Close to 146C; edges, close to 138B. Stipules: Quantity and appearance: Two leafy stipules, opposite, at the petiole attachment to the stem. Length: About 9 mm. Width: About 1.3 cm. Shape, in overall outline: Broadly obovate; occasionally cleft with one to three shallow incisions distally. Texture and luster, upper surface: Densely pubescent; matte. Texture and luster, lower surface: Densely pubescent; slightly glossy. Color, upper surface: Close to NN137A to NN137B. Color, lower surface: Close to 147B.

Inflorescence description:

*Appearance*.—Anemone-type inflorescence form with narrowly obovate-shaped ray florets and tubular disc florets; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 52 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 31 inflorescences develop per flowering stem.

*Inflorescence size*.—Diameter, grown as a spray-type: About 7.3 cm. Depth (height), grown as a spray-type: About 2.8 cm. Disc diameter, grown as a spray-type: About 4.5 cm.

*Receptacles*.—Height: About 5 mm. Diameter: About 9 mm. Shape: Flattened globular. Color: Close to 145B and 145C.

*Inflorescence buds*.—Height: About 1.7 cm. Diameter: About 1.5 cm. Shape: Broadly oblong. Texture and luster: Distally, smooth and glabrous; proximally, moderately pubescent; slightly glossy. Color: Developing involucral bracts, close to 137C, 138B and 138C; developing ray florets, close to 164C.

*Ray florets*.—Quantity and arrangement: About 30 arranged in about two whorls. Length: About 3.6 cm. Width: About 1.2 cm. Shape: Narrowly obovate; moderately concave to straight and flat with development; slightly carinate. Apex: Shallowly emarginate to close to obtuse. Base: Attenuate. Margin: Entire; not undulate. Aspect: About 35° to 45° from vertical. Texture and luster, upper surface: Smooth, glabrous; slightly velvety; matte. Texture and luster, lower surface: Smooth, glabrous; slightly glossy. Color: When opening, upper surface: Close to 164C, 167B and N167C. When opening, lower surface: Close to 162B. Fully opened, upper surface: Close to 24C; towards the apex, slightly tinged with close to 168D and 171D; towards the base, close to 22B and 22C; venation, similar to lamina colors; color does not change with subsequent development. Fully opened, lower surface: Close to 162C; venation, close to 162B; color does not change with subsequent development.

*Disc florets*.—Quantity and arrangement: About 190 at the center of the receptacle. Length: About 2.3 cm. Diameter: About 4 mm. Shape: Lower 75% fused into a tube; upper 25% free. Apex: Bluntly acute. Margin, free-part: Entire. Texture and luster, inner surface: Smooth, glabrous; matte. Texture and luster, outer surface: Smooth, glabrous; slightly glossy. Color, when opening, inner and outer surfaces: Close to 1B; distally, close to 1A. Color, fully opened, inner surface: Close to 20A; towards the base, close to 19A. Color, fully opened, outer surface: Close to 160B; towards the apex, close to 160A.

*Involucral bracts*.—Quantity and arrangement: About 24 arranged in about two whorls. Length: About 1 cm. Width: About 4 mm. Shape: Ovate to narrowly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to 143A and 143B; lateral margins, translucent and close to 157D and apical margins tinged with close to 199B to 199C. Color, lower surface: Close to 143A; lateral margins, translucent and close to 157D and apical margins tinged with close to 199B to 199C.

*Peduncles*.—Length, terminal peduncle: About 3.8 cm. Diameter, terminal peduncle: About 4 mm. Length, third peduncle: About 4.9 cm. Diameter, third peduncle: About 3.5 mm. Strength: Strong. Aspect, terminal peduncle: Upright. Aspect, third peduncle: About 40° from the flowering stem axis. Texture and luster: Densely pubescent; slightly glossy. Color: Close to 138A.

*Reproductive organs*.—Androecium: Present on disc florets only. Quantity: About two per floret. Filament length: About 2 mm. Filament color: Close to 145B. Anther size: About 0.4 mm by 1 mm. Anther shape: Narrowly oblong. Anther color: Close to 13A. Pollen amount: None observed. Gynoecium: Present on both ray and disc florets. Quantity: One per floret. Pistil length: About 6 mm. Style length: About 5.5 mm. Style color: Close to 145C. Stigma diameter: About 1 mm. Stigma shape: Cleft to three-parted, decurrent. Stigma color: Close to 153D. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* Wilt (*Fusarium oxysporum* spp. *chrysanthemi* (strain FoNL1)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFHOLA6' as illustrated and described.

* * * * *